United States Patent [19]

Okano et al.

[11] Patent Number: 5,284,766
[45] Date of Patent: Feb. 8, 1994

[54] BED MATERIAL FOR CELL CULTURE

[75] Inventors: Teruo Okano, Ichikawa; Kazunori Kataoka, Kashiwa; Noriko Yamada, Itabashi; Yasuhisa Sakurai, Suginami; Takayuki Amiya; Akira Mamada, both of Wakayama, all of Japan

[73] Assignees: Kao Corporation; Tokyo Women's Medical College, both of Tokyo, Japan

[21] Appl. No.: 817,954

[22] Filed: Jan. 7, 1992

Related U.S. Application Data

[63] Continuation of Ser. No. 476,549, Feb. 7, 1990, abandoned.

[30] Foreign Application Priority Data

Feb. 10, 1989 [JP] Japan .................................. 1-31844

[51] Int. Cl.$^5$ .......................... C12N 5/06; C12N 5/00
[52] U.S. Cl. .......................... 435/240.23; 435/240.243
[58] Field of Search .................. 435/240.23, 240.243, 435/182

[56] References Cited

U.S. PATENT DOCUMENTS 4,912,032 3/1990 Hoffman et al. .................. 435/7.1
4,975,375 12/1990 Haruta et al. .................. 435/182

FOREIGN PATENT DOCUMENTS 59-95930 6/1984 Japan .
62-06682 1/1987 Japan .
8808448 11/1988 PCT Int'l Appl. .

OTHER PUBLICATIONS

Patent Abstracts of Japan, vol. 8, No. 205 (C-243) [1642], Sep. 19, 1984; & JP-A-59 95 930 Kogyo Gijutsuin (Japan) Feb. 6, 1984 * The entire abstract *.
Chemical Abstracts, vol. 107, No. 17, Oct. 26, 1987, p. 339, abstract No. 150296t, Columbus, Ohio, US; & JP-A062 06 682 (Canon K.K.) Jan. 13, 1987 * The entire abstract *.

Primary Examiner—George C. Elliott
Attorney, Agent, or Firm—Wenderoth, Lind & Ponack

[57] ABSTRACT

Disclosed is a bed material whereby cultured or grown cells are collected or detached from the material without a proteolysis enzyme or chemical material. The bed material comprises a support and a coating thereon, wherein the coating is formed from a polymer or copolymer which has a critical solution temperature to water within the range of 0° C. to 80° C.

6 Claims, No Drawings

BED MATERIAL FOR CELL CULTURE

This application is a continuation of application Ser. No. 07/476,549, filed Feb. 7, 1990, now abandoned.

FIELD OF THE INVENTION

The present invention relates to a bed material for cell culture in the field of biology, medical science, immunology and the like.

BACKGROUND OF THE INVENTION

Hitherto, culturing cells has been conducted on a surface of glass or a surface-treated synthetic polymer. For example, a polystyrene which has been subjected to a surface treatment, e.g. γ ray irradiation, silicon coating etc., is used as a bed material for cell culture. Cultured cells on the bed are collected or detached from the surface of the bed by treating with a proteolysis enzyme (e.g. trypsin) or a chemical material (e.g. EDTA). In the treatment with a proteolysis enzyme or chemical material, however, the following problems occurred: (1) the treating process is complicated and there is high possibility of introducing impurities. (2) The cultured or grown cells are adversely affected by the treatment and the treatment may harm their inherent functions.

SUMMARY OF THE INVENTION

In order to overcome the above mentioned problems, the present invention provides a bed material from which cultured or grown cells are collected or detached without a proteolysis enzyme or chemical material. The bed material of the present invention comprises a support and a coating thereon, wherein the coating is formed from a polymer or copolymer which has a critical solution temperature to water within the range of 0° C. to 80° C.

DETAILED DESCRIPTION OF THE INVENTION

The critical solution temperature is defined as follows. When a certain material is mixed with water, the mixture is divided into two layers at a particular temperature because of its poor solubility, but eventually the material is completely dissolved with water to turn it to a uniform solution if it is either heated or cooled beyond a certain temperature. The certain temperature is defined as "critical solution temperature". If the uniform solution is formed when heated, the critical solution temperature is called "upper critical solution temperature". If the uniform solution is formed when cooled, it is called the "lower critical solution temperature".

It is generally known that the critical solution temperature is obtained by making a solution phase diagram in respect to water (ion exchanged water or distilled water). For making the solution phase diagram, mixtures of a polymer to be measured and water in various concentrations (such as weight %, volume %, molar %, molar ratio etc.) are prepared and the mixtures are heated or cooled to observe the conditions of the mixture. The conditions are determined by art-known methods, such as (a) by observing with the eyes, (b) observing the critical opalescence, (c) observing the scattered light strength, and (d) observing the transmitted laser light and the like.

The polymer or copolymer of the present invention should have either an upper or lower critical solution temperature within the range of 0° C. to 80° C., preferably 20° to 50° C. If it is higher than 80° C., cultured or grown cells may die. If it is lower than 0° C., the growth rate of the cells may be very much lowered or the cells may die.

The polymer or copolymer of the present invention may be prepared by polymerizing or copolymerizing some hydrophilic monomers. Non-limiting examples of the monomers, provided that a parenthesis indicates a lower critical solution temperature of homopolymer, are represented by a (meth)acrylamide, such as acrylamide, methacrylamide, etc.; an N-substituted (meth)acrylamide, such as N-ethyl acrylamide (72° C.), N-n-propyl acrylamide (21° C.), N-n-propyl methacrylamide (27° C.), N-isopropyl acrylamide (32° C.), N-isopropyl methacrylamide (43° C.), N-cyclopropyl acrylamide (45° C.), N-cyclopropyl methacrylamide (60° C.), N-ethoxyethyl acrylamide (about 35° C.), N-ethoxyethyl methacrylamide (about 45° C.), N-tetrahydrofurfuryl acrylamide (about 28° C.), N-tetrahydrofurfuryl methacrylamide (about 35° C.) etc.; N,N-di-substituted (meth)acrylamide, such as N,N-dimethyl (meth)acrylamide, N,N-ethylmethyl acrylamide (56° C.), N,N-diethyl acrylamide (32° C.), 1-(1-oxo-2-propenyl)-pyrrolidine (56° C.), 1-(1-oxo-2-propenyl)-piperidine (about 6° C.), 4-(1-oxo-2-propenyl)-morpholine, 1-(1-oxo-2-methyl-2-propenyl)-pyrrolidine, 1-(1-oxo-2-methyl-2-propenyl)-piperidine, 4-(1-oxo-2-methyl-2-propenyl)-morpholine etc.; a vinyl ether, such as methyl vinyl ether (35° C.); and the like. A copolymer of the above listed monomers or other monomers, a graft polymer or copolymer or a mixture of the polymers can also be employed in the present invention, in order to adjust the critical solution temperature, depending upon the type of cells, to enhance an interaction between the support and the coating thereon or to control the balance between the hydrophilic and hydrophobic properties of the bed material. The polymer or copolymer of the present invention may be crosslinked unless the inherent properties of the polymer would be deleteriously affected thereby.

The support of the present invention can be prepared from any material, for example polymers (e.g. polystyrene, poly(methyl methacrylate) etc.), ceramics, metals, glass and modified glass. The shape of the support is not limited, but typically a Petri dish, a plate, a fiber, particles, and any type container can be used for the cell culture (e.g. a flask).

A polymer or copolymer can be bound on the support by a chemical method or by a physical method. In the chemical method an electron beam, γ ray irradiation, ultraviolet irradiation, corona treatment and plasma treatment can be used. In case where the support and the coating have groups reactive with each other, an organic reaction (e.g. a radical, anionic or cationic reaction) can also be used. In the physical method, the polymer per se or a combination of the polymer and a matrix compatible with the support is coated on the support, thus binding by physical absorption power. Examples of the matrix are graft or a block copolymers of the polymer to be coated, with the monomer forming the support or other monomers compatible with the support.

In order to collect or detach the grown or cultured cells, the bed material is either heated or cooled to exceed the upper or lower critical solution temperature, thus detaching the cells, and rinsed with an isotonic solution to collect the cells.

The function of the present invention will be illustrated by adopting poly(N-isopropyl acrylamide) as an example. It is known that poly(N-isopropyl acrylamide) has a lower critical solution temperature of about 32° C. in water. The monomer, i.e. N-isopropyl acrylamide, is polymerized on a polystyrene Petri dish for cell culture by irradiating electron beams. At temperatures higher than 32° C., the poly(N-isopropyl acrylamide) coating is hydrophobic and expels water molecules inside the coatings, which results in a reduced volume. At temperatures lower than 32° C., the coating is hydrophilic and holds water molecules to result in swelling.

According to the present invention, the surface of the bed material reversibly changes from hydrophilic to hydrophobic, and vice versa, by controlling the temperature. Accordingly, the grown or cultured cells are detached from the bed material by simply controlling the temperature without destroying the cells, and then rinsed with an isotonic solution to collect the cells. Since the bed material of the present invention does not employ a proteolysis enzyme (trypsin) and a chemical material (EDTA), the detaching or removing process is simplified and virtually no impurities are introduced. The bed material of the present invention is such as not to injure the cells and is such as to protect the inherent functions of the cells.

EXAMPLES

The present invention is illustrated by the following examples which, however, are not to be construed as limiting the invention to the details thereof.

Examples 1 to 3

A Petri dish (available from the Becton Dickinson Labware Co., Ltd. as FALCON 3001) was employed as a support and the cells to be cultured are bovine aorta endothelial cells. N-isopropyl acrylamide was dissolved in isopropyl alcohol in the concentration shown in Table 1 and coated on the Petri dish. It was then irradiated with an electron beam in the irradiation dose shown in Table 1 to form a poly(N-isopropyl acrylamide) coating. The coated Petri dish was rinsed with ion-exchanged water to remove the remaining monomers and dried in a clean bench.

The culturing of bovine aorta endothelial cells was carried out at 37° C. in 5% carbon dioxide using a Dulbecco's modified Eagle's medium (DMEM) containing a 20% fetal calf serum (FCS) on the obtained Petri dish. After growing cells, the Petri dish was cooled to 4° C. and allowed to stand to detach the cells. A collection % of the grown cells (number of cells collected by detaching/number of cells to be grown X 100) was calculated and the results are also shown in Table 1.

Examples 4 and 5

A coated Petri dish was prepared as generally described in Examples 1 to 3, with the exception that N,N-diethyl acrylamide was employed in the concentration shown in Table 1 instead of N-isopropyl acrylamide, and the experiment of Examples 1 to 3 was repeated. A collection % of grown cells is shown in Table 1.

Comparative Examples 1 to 3

In Comparative Example 1, no surface coating was conducted on the Petri dish and an experiment was done as generally described in Example 1.

In Comparative Examples 2 and 3, an electron beam was irradiated on the same Petri dish which was not coated with any monomer solution, and an experiment was done as generally described in Example 1. A collection % of grown cells is shown in Table 1.

TABLE 1

|  | Concentration of monomer or polymer | Irradiation dose of electron beam (Mrad) | Collection % of grown cells |
|---|---|---|---|
| Example |  |  |  |
| 1 | N-isopropyl acrylamide 1 wt % | 5 | >90% |
| 2 | Poly(N-isopropyl acrylamide) 1 wt % | 5 | >90% |
| 3 | N-isopropyl acrylamide 10 wt % | 25 | >90% |
| 4 | N,N-diethyl acrylamide 1 wt % | 5 | >90% |
| 5 | N,N-diethyl acrylamide 10 wt % | 5 | >90% |
| Comp. EX. 1 | 0 | 0 | Detachment and collection are impossible |
| Comp. Ex. 2 | 0 | 5 |  |
| Comp. Ex. 3 | 0 | 25 |  |

In the above Examples and Comparative Examples, a contact angle was determined by an under water method using a FACE Contact Angle Meter CA-D (available from Kyowa Surface Chemistry Co., Ltd.) and the results are shown in Table 2.

TABLE 2

|  | Contact angle at 37° C. | Contact angle at 4° C. |
|---|---|---|
| Example |  |  |
| 1 | 42 | 25 |
| 2 | 48 | 28 |
| 3 | 36 | 22 |
| 4 | 44 | 24 |
| 5 | 46 | 26 |
| Comparative Example |  |  |
| 1 | 58 | 64 |
| 2 | 56 | 62 |
| 3 | 56 | 62 |

Example 6

A coated Petri dish was prepared as generally described in Examples 1 to 3, with the exception that N-ispropyl methacrylamide was employed in the concentration shown in Table 3 instead of N-isopropyl acrylamide. Bovine aorta endothelial cells were cultured at 45° C. and cooled to 30° C. at which the cells were detached from the dish. A collection % of grown cells is shown in Table 3.

Example 7

A coated Petri dish was prepared as generally described in Examples 1 to 3, with the exception that N-n-propyl acrylamide was employed in the concentration shown in Table 3 instead of N-isopropyl acrylamide. Bovine aorta endothelial cells were cultured at 25°

C. and cooled to 10° C. at which the cells were detached from the dish. A collection % of grown cells is shown in Table 3.

TABLE 3

|  | Monomer concentration | Irradiation dose of electron beam (Mrad) | Collection % of grown cells |
| --- | --- | --- | --- |
| Example 6 | N-n-propyl acrylamide 10% by weight | 25 | >90% |
| Example 7 | N-isopropyl acrylamide 10% by weight | 25 | >90% |

Example 8

This example confirms the degree of injury of the detached cells. The detached cells of Example 3 were centrifuged at 600 G for 5 minutes to collect $1 \times 10^5$ cells which were then cultured on a FALCON 3001 Petri dish. The culturing process was the same as Example 3. After 4 days, the number of cells were counted and the result is shown in Table 4.

Comparative Example 4

The cells cultured or grown in Comparative Example 1 were treated with a 0.05% trypsin—0.02% EDTA solution to detach them. The detached cells were centrifuged at 600 G for 5 minutes to collect $1 \times 10^5$ cells which were then cultured on a FALCON 3001 Petri dish as generally described in Example 1. After four days, number of cells were counted and the result is shown in Table 4.

TABLE 4

|  | Number of cells when culturing started | Number of cells after 4 days |
| --- | --- | --- |
| Example 8 | $1 \times 10^5$ | $1 \times 10^6$ |
| Comp. Ex. 4 | $1 \times 10^5$ | $5 \times 10^5$ |

As is apparent from the above Examples and Comparative Examples, in the polystyrene Petri dish which was coated with poly(N-isopropyl acrylamide) or poly(N,N-diethyl acrylamide), the contact angle decreased by changing from 37° C. to 4° C., as shown in Table 2. This shows that the coating on the dish changes from hydrophobic to hydrophilic. In Examples 1 to 5 in which the coated Petri dishes were employed, the cultured cells were easily detached from dishes when cooled, as shown in Table 1.

On the other hand, in the case where such a coating is not coated, the contact angle is not changed when cooled, as shown in Table 2, thus the surface maintains its hydrophobic condition. If an uncoated dish is employed, the detachment of the cultured cells was not observed.

As to the degree of injury of the cultured cells, Example 8 could grow 10 times more than that of the starting point, but Comparative Example 4 could grow only 5 times more. This shows that the degree of injury is smaller than that of conventional ones.

What is claimed is:

1. A method for culturing cells, which comprises coating a support with a polymer or copolymer which has a lower or upper critical solution temperature to water within the range of 0° to 80° C., culturing cells attached to the surface thereof at a higher temperature than said lower critical solution temperature or at a lower temperature than said upper critical solution temperature on said coated surface having hydrophobic properties and detaching and collecting the cultured cells from said coated surface by changing the temperature to a lower temperature than said lower critical solution temperature or at a higher temperature than said upper critical solution temperature, thereby changing the properties of said coated surface from hydrophobic to hydrophilic.

2. A method for culturing cells according to claim 1 wherein said polymer or copolymer has a lower or upper critical solution temperature to water with the range of 0° to 50° C.

3. A method for culturing cells according to claim 1 wherein said polymer or copolymer has a lower or upper critical solution temperature to water within the range of 20° to 50° C.

4. A method for culturing cells according to claim 1 wherein said polymer or copolymer is selected from the group consisting of poly(N-isopropyl acrylamide), poly(N-isopropyl methacrylamide), poly(N-n-propyl acrylamide) and poly(N,N-diethyl acrylamide).

5. A method for culturing cells according to claim 1 wherein said support is prepared from polystyrene or glass.

6. A method for culturing cells according to claim 1 wherein said support is a Petri dish.

* * * * *